United States Patent
Gallis et al.

(10) Patent No.: US 6,946,119 B2
(45) Date of Patent: Sep. 20, 2005

(54) PRECIPITATED SILICA PRODUCT WITH LOW SURFACE AREA, DENTIFRICES CONTAINING SAME, AND PROCESSES

(75) Inventors: Karl W. Gallis, Belcamp, MD (US); Fitzgerald A. Sinclair, Bear, DE (US); Mark E. Wozniak, Bel Air, MD (US); Jason T. Zapf, Perryville, MD (US); John A. Kostinko, Bel Air, MD (US); Michael Simone, North East, MD (US)

(73) Assignee: J.M. Huber Corporation, Edison, NJ (US)

( * ) Notice: Subject to any disclaimer, the term of this patent is extended or adjusted under 35 U.S.C. 154(b) by 301 days.

(21) Appl. No.: 10/366,604

(22) Filed: Feb. 14, 2003

(65) Prior Publication Data

US 2004/0161389 A1 Aug. 19, 2004

(51) Int. Cl.⁷ .............. A61K 7/16; A61K 7/18; A61K 7/22; C01B 33/12
(52) U.S. Cl. .............. 424/49; 424/52; 424/54; 516/82; 516/113; 423/335; 423/339; 51/308
(58) Field of Search .............. 424/49, 52, 54; 516/82, 113; 423/335, 339; 51/308

(56) References Cited

U.S. PATENT DOCUMENTS

| | | |
|---|---|---|
| 2,601,235 A | 6/1952 | Alexander et al. |
| 2,731,326 A | 1/1956 | Alexander et al. |
| 2,885,366 A | 5/1959 | Iler |
| 5,266,306 A | 11/1993 | Ohtsuki et al. |
| 5,447,704 A | 9/1995 | Aldcroft et al. |
| 5,897,849 A | 4/1999 | Alcaraz et al. |
| 5,968,470 A | 10/1999 | Persello |
| 6,159,277 A | 12/2000 | Tanaka et al. |
| 6,294,106 B1 | 9/2001 | Pryor |
| 6,342,193 B1 | 1/2002 | Tanaka et al. |
| 6,365,522 B1 | 4/2002 | Pryor |
| 6,471,948 B1 | 10/2002 | Adamy et al. |

FOREIGN PATENT DOCUMENTS

| | | | |
|---|---|---|---|
| EP | 0 236 070 B1 | 3/1992 | |
| EP | 0 666 832 B2 | 7/2002 | |
| WO | WO 93/23007 | * 11/1993 | ............ A61K/7/22 |

* cited by examiner

*Primary Examiner*—Frederick Krass
(74) *Attorney, Agent, or Firm*—Carlos Nieves; William Parks

(57) ABSTRACT

Precipitated silica product having low surface area and enhanced flavor compatibility. The precipitated silica product is especially well-adapted for use in dentifrices containing cetylpyridinium chloride, which do not attach to the low surface area silica product in a meaningful level and thus remain available for antimicrobial action. Processes for making the low surface area silica product are also provided.

33 Claims, 2 Drawing Sheets

PRECIPITATED SILICA PRODUCT WITH LOW SURFACE AREA, DENTIFRICES CONTAINING SAME, AND PROCESSES

BACKGROUND OF THE INVENTION

1. Field of the Invention

This invention relates to precipitated amorphous silica having low surface area and enhanced flavor compatibility, and processes for making it. The precipitated silica is especially well-adapted for use in dentifrices containing cetylpyridinium chloride.

2. Description of the Related Art

Modern dentifrices often contain an abrasive substance for controlled mechanical cleaning and polishing of teeth, and optionally a chemical cleaning agent, among other common ingredients, such as humectants, flavors, therapeutic ingredients, such as an anticaries agent, rheology control agents, binders, preservatives, colors, and sudsing agents, among others. Oral care products also often contain therapeutic agents, such as anti-microbial agents. Cetylpyridinium chloride ("CPC") is an anti-microbial agent used for this purpose, such as in mouthwashes and toothpastes. There is an increased desire among dentifrice manufacturers to incorporate anti-microbial agents in dentifrice applications for the control of malodor and/or other therapeutic action, with CPC being one of the more favored. It is cost effective and generally recognized as safe. By contrast, some alternative anti-microbial agents currently being used in dentifrices have come under increasing scrutiny for possible contribution to the increased resistance of some bacterial strains to antibiotics. CPC is not considered to contribute to this health problem.

CPC is a cationic ("positively") charged compound. CPC's antimicrobial action is generally understood to result from its ability to bind to anionically ("negatively")-charged protein moieties on bacterial cells present in the mouth. This CPC attachment mechanism results in a disruption of normal cellular function of bacteria and contributes to the prevention of plaque formation and other bacterial actions.

A problem encountered in CPC usage in dentifrices has been that CPC tends to indiscriminately bind to negatively-charged surfaces. In particular, co-ingredients of toothpaste formulations having negatively-charged surfaces also may bind to CPC before it performs any antimicrobial action. Once bound to these nontargeted surfaces, the CPC is generally unavailable to perform any meaningful antimicrobial action.

In this regard, silica is often used as an abrasive in dentifrices. For instance, silica's abrasive action is used for pellicle removal from teeth. Most conventional silicas used in dentifrices have negatively-charged surfaces. Consequently, CPC adsorbs onto such conventional silica powders. For reasons explained above, the adsorption of CPC upon silica or other co-ingredients of the dentifrice is highly undesirable.

U.S. Pat. No. 6,355,229 describes a CPC compatible dentifrice formulation containing guar hydroxypyropyltrimonium chloride. The guar complex has a higher affinity toward binding to negatively-charged species. It preferentially binds to anionic components leaving CPC free to bind to plaque.

U.S. Pat. No. 5,989,524 describes a silica that is compatible with flavors obtained by treating the surface of the silica originating from the reaction of an alkali metal silicate with an inorganic or organic acidic agent with the aid of an organic compound capable of developing hydrogen or ionic bonds with the Si—OH silanol groups or the SiO anionic groups at the silica surface. The organic agent can be added to the silica in the form of slurry before or after salts are removed, or can be sprayed on to dry silica.

A number of patent publications describe processes for making composite synthetic silica particles, including the following.

U.S. Pat. No. 2,731,326 describes a process of preparing xerogels in which a silica gel is stabilized so that the pores of the gel do not collapse upon drying. It involves a two-stage precipitation process where in the first stage silica gel is formed, and in the second stage a layer of dense amorphous silica is formed over the gel particles in order to provide sufficient reinforcement such that the pores do not collapse upon drying. The gel particles have a particle size in the range of 5 to 150 millimicrons (nm), and preferably have an average diameter of from 5 to 50 millimicrons. The resulting reticulated particles can be dewatered and dried into powder form. The '326 patent states that when silica particles have a specific surface area of greater than 200 $m^2/g$, it is preferred to replace the water with an organic liquid, and then dehydrate the silica particles. The '326 patent describes silica products with preferred specific surface areas 60 to 400 $m^2/g$. The '326 patent indicates little advantage is obtained in carrying the process of accretion to an extreme. The preferred products of the '326 patent process of accretion are limited so that the original dense ultimate units of the aggregates do not lose their identity and the original aggregates structure is not obscured.

U.S. Pat. No. 2,885,366 describes a process used to deposit a dense layer of silica over particles other than silica.

U.S. Pat. No. 2,601,235 describes a process for producing built-up silica particles in which a silica sol heel is heated above 60° C. to make nuclei of high molecular weight silica. The nuclei is mixed with an aqueous dispersion of active silica made by acidulating alkali metal silicate, and the mixture is heated above 60° C. at a pH of 8.7 to 10, such that active silica accretes to the nuclei.

U.S. Pat. No. 5,968,470 describes a process to synthesize silica having controlled porosity. It involves the addition of silicate and acid to a solution of colloidal silica with or without an electrolyte added (salt). The porosity can be controlled based upon the amount of colloidal silica added in the first step of the reaction. Silica with BET surface areas ranging from 20 to 300 $m^2/g$, CTAB specific surface areas from 10 to 200 $m^2/g$, oil absorption (DBP) ranging from 80 to 400 $m^2/g$, pore volumes from 1 to 10 $cm^3/g$, and mean pore diameters from 10 to 50 nm could be synthesized. The intended use of materials produced by this process is in the paper and catalysis marketplace.

U.S. Pat. No. 6,159,277 describes a process for the formation of silica particles with a double structure of a core of dense amorphous silica and a shell of bulky amorphous silica. A gel is formed in a first step. The gel is then aged, wet pulverized, and then sodium silicate is added in the presence of an alkali metal salt in order to form amorphous silica particles on the surface of the milled gel particles. The resultant double structure silica material has an average particle diameter of 2 to 5 micrometers and a surface area of 150 to 400 $m^2/g$. The resultant material is said to have improved properties for use in as a delustering agent in paint and coatings.

Patent publications that describe use of silicas in dentifrice or oral cleaning compositions include the following.

U.S. Pat. No. 5,744,114 describes silica particles adopted for formulation into dentifrice compositions having a unique surface chemistry as to be at least 50% compatible with zinc values, and have a number of OH functions, expressed as $OH/nm^2$, of at most 15 and a zero charge point of from 3 to 6.5. The '114 patent describes a process of preparing silica particles by the reaction of silicate with an acid to form a suspension or gel of silica. The gel/suspension is then separated, washed with water and treated with acid to adjust the pH below 7.

U.S. Pat. No. 5,616,316 describes silica that is more compatible with customary dentifrice ingredients. In addition to many other ingredients, cationic amines are mentioned.

Another problem associated with usage of conventional silicas in dentifrices is that they often have flavor compatibility problems. That is, the conventional silicas tend to interact with flavorants included in the same dentifrice in a manner that creates off-flavors, making the product less palatable. This off-flavor problem accompanying use of some conventional silicas in dentifrices is highly undesirable from a consumer satisfaction standpoint.

A need exists for silicas that can be used together with anti-microbial agents such as CPC in oral cleaning compositions such as dentifrices without impairing the respective functions of either ingredient. Silicas that are more flavor compatible are also in need. In general, the low surface area silica disclosed in this invention may be useful whenever it is desirable to limit the interaction of the silica particulate with desirable additives and components found in dentifrice formulations. The present invention meets these needs and others as will become readily apparent from the disclosure that follows.

SUMMARY OF THE INVENTION

This invention relates to a unique low surface area silica product. This silica product is particularly useful in dentifrice compositions containing cetylpyridinium chloride ("CPC") or other therapeutic agents. CPC does not appreciably bind to these low surface area silica products. Therefore, when contained in a dentifrice composition, an increased amount of CPC remains available for its antimicrobial duties while the silica abrasive remains unimpaired by CPC attachment, and able to provide the mechanical cleaning and polishing action common to abrasive silica products. Additionally, the low surface area silica product is highly compatible with many dentifrice flavorants. The inventive silica product reduces the possibility of off-flavors when present together with flavorants. Also, the low surface area silica product is highly compatible with fluoride ion sources such as sodium fluoride. The low surface area silica product does not adversely interact with or impair those anticaries agents or their function.

Dentifrices that contain this silica product offer the benefit that CPC also can be used which remains at an effective antibacterial level in the dentifrice despite the presence of silica abrasive. As another benefit and advantage, dentifrices containing the low surface area silica product have superior flavor attributes. The flavor compatibility of the low surface area silica product of this invention is superior to current commercial dental-grade silica materials, as has been demonstrated in experiments described herein. In this respect, the inventive precipitated silica product generally has a % CPC Compatibility value of at least 20%, particularly greater than 40%, and more particularly greater than 60%, and even more particularly greater than 70%. The "% CPC Compatibility" characteristic of the silica is determined by a testing procedure explained in the more detailed descriptions provided below.

In one aspect, the invention relates to a precipitated silica product comprising surface-treated silica particulate including silica particles having a median diameter of 1 to 100 micrometers that supports deposits of a relatively denser amorphous "active" silica material at particulate surfaces in an amount effective to provide a BET specific surface area of from 1 to 50 square meters per gram, preferably 1 to 40 square meters per gram, more preferably less than 30 square meters per gram, and in amount effective to reduce attachment of CPC thereto as compared to the silica particulate without the surface deposits. In one particular aspect, the silica particulate is in the form of silica aggregates or agglomerates formed of the silica particles.

The inventive low surface area silica product may be produced via process including at least the steps of providing silica particulate as a preformed material or forming it in-situ, followed by precipitating active silica upon the silica particulate effective to satisfy the specific surface area and reduced CPC attachment requirements described elsewhere herein. The denser silica material deposited on the silica particulate "coats" the underlying silica substrate particulate primarily in the sense that it penetrates into and/or blocks the opening of the pores of the underlying silica particulate to effectively reduce the surface area of the silica particulate substrate.

The oral cleaning compositions that can be benefited by incorporation of the low surface area silica product of this invention include, for example, dentifrices, chewing gums, and mouthwashes, and the like. The term "dentifrice" means oral care products in general such as, without intending to be limited, toothpastes, tooth powders, and denture creams. The low surface area silica particulate of the invention also have wider cleaning utility and application, including, for instance, as a metal, ceramic or porcelain cleaning or scrubbing agent.

For purposes herein, the term "silica particulate" means finely divided silica, and the term encompasses silica primary particles, silica aggregates (i.e., unitary clusters of a plurality of silica primary particles), silica agglomerates (i.e., unitary clusters of a plurality of silica aggregates), singly or in combinations thereof. The term "denser", as used in herein, refers to a lower porosity silica particulate. Quantitative BET surface area measurements taken before and after deposition of the active silica on the silica substrate particulate can be compared to determine qualitatively if a less porous (i.e., more dense) particulate has been created, i.e., as indicated by a measurable reduction (not increases or absence of change) in the specific surface area value.

DETAILED DESCRIPTION OF THE PREFERRED EMBODIMENTS

Figure 1:
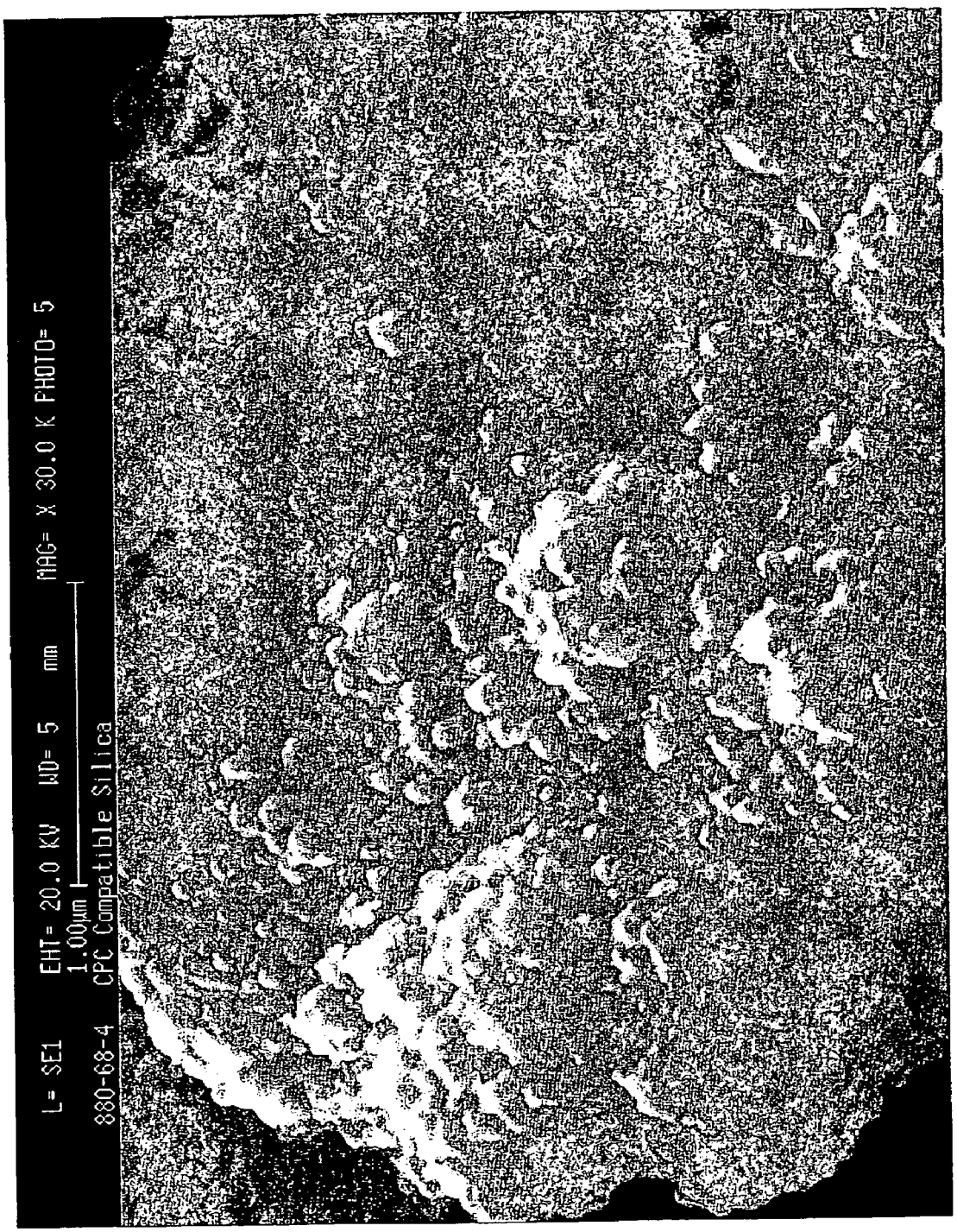
FIG. 1 is an SEM of a surface-treated silica made according to Example 3 described herein.

In accordance with the preceding summary, the present invention is directed to a unique low surface area silica product, which is particularly useful in dentifrice compositions containing therapeutic agents, such as CPC. The low surface area silica product of the present invention limits the ability of CPC to bind to these products. Consequently, loss of CPC to inadvertent interaction to silica abrasive is minimized.

The low surface area silica product may be produced by a general process scheme, in which:

1) a slurry of amorphous silica particulate is provided either by slurrying up a prefabricated silica material obtained in dry finely divided form, or alternatively from an ongoing production run in which fresh precipitated silica is in slurry or wet cake form without ever having been dried into powder form, followed by;

2) precipitating active silica upon the substrate silica particulate effective to satisfy the specific surface area and reduced CPC interaction requirements described herein.

Sourcing of Silica Particulate "Substrate" Material

Regarding the silica particulate provision of above general step 1), an amorphous silica particulate is provided. If provided in dry form, the dried crude silica used as the "particulate" to be surface-modified according to this invention includes commercially obtainable precipitated silicas, such as Zeodent® 113, Zeodent® 115, Zeodent® 153, Zeodent® 165, Zeodent® 623, Zeodent® 124 silicas, and so forth, which are available from J.M. Huber Corporation. These commercially available silicas typically are in aggregate form.

The dry finely divided silica particulate also may be obtained from a supply of premanufactured material made earlier at the same or different production facility where procedures used for the surface area reduction step can be performed at a later time.

The dry precipitated silicas to be used as the substrate particulate for the surface area reduction operation generally should have a median particle size of 1 to 100 $\mu$m, a BET specific surface area value of approximately 30 to 100 $m^2/g$, and a linseed oil absorption of approximately 40 to 250 ml/100 g. Zeodent® 113, for example, typically has a median particle size of approximately 10 $\mu$m, BET surface area value of approximately 80 $m^2/g$, a linseed oil absorption of approximately 85 ml/100 g. The silica particulates used as the substrate material for the coating operation, described below, preferably are constituted of silica particles having a median diameter of 1 to 100 micrometers. Substrate materials, such as high structure precipitated silica, silica gels and pyrogenic silica, with BET surface area greater than 100 $m^2/g$, such as about 100 to 800 $m^2/g$, or linseed oil absorption greater than 120 ml/100 g, such as about 120 to 400 ml/100 g, can be used in the present invention, although longer surface area reduction times (active silica deposition times) will be required to lower the BET surface area to desired levels.

The dry precipitated silicas must be slurried in an aqueous medium before they can be subjected to the dense silica coating application procedure described herein. Generally, the dry silicas are slurried to a solids content that creates a pumpable mixture, generally of from about 1 to about 50%.

Alternatively, crude undried liquid phase silica materials can be prepared in situ during a common production run scheme as the surface area reduction operation. Alternatively, a crude silica wet cake can be stored for later slurrying, or stored as a slurry thereof, until the surface area reduction procedure is performed at a subsequent time, without ever drying the silica solids to powder form. The solids content of the slurry provided before the surface area reduction operation is performed will be the same as that described above in connection with the dry silicas.

The liquid phase source of precipitated silicas generally should have constituent particle sizes, overall particle size, BET specific surface area value, and linseed oil absorption properties comparable to those respective values described above in connection with the dry source form of the silica. To the extent they meet those physical criteria, the liquid phase silicas can include amorphous precipitated silicas, silica gels or hydrogels pyrogenic silica and colloidal silicas. In one aspect, the silica particulates provided in situ are in aggregate or agglomerate form.

The silicas can be produced by acidulating an alkali metal silicate with a mineral acid, such as sulfuric acid, or organic acid, with heating. Synthetic amorphous precipitated silicas are generally prepared by admixing alkaline silicate solutions with acids with heating, stirring, and then filtering or centrifuging to isolate the precipitated silica solids as a wet cake form thereof. The reaction media may optionally contain an electrolyte, such as sodium sulfate. Wet cake of silica generally contains about 40 wt % to about 60 wt % water, and the remainder is principally solids. The precipitated reaction mass generally is filtered and washed with water to reduce the $Na_2SO_4$ levels to tolerable levels. Washing of the reaction product is generally conducted after filtering. The pH of the washed wet cake can be adjusted, if necessary, prior to proceeding to subsequent steps described herein. If necessary, the washed wet cake is slurried to a solids content of between 1 to 50% before the surface area reduction procedure is performed on it. As previously noted, if the silica is dried, or dried and comminuted to a desired size, it must be reslurried before the surface area reduction procedure can be conducted on the crude silica.

To the extent they meet other requirements discussed herein, the crude silica to be used as a source of the substrate particulate for surface area reduction described herein can be, for example, precipitated silicas made as described in U.S. Pat. Nos. 4,122,161, 5,279,815 and 5,676,932 to Wason et al., and U.S. Pat. Nos. 5,869,028 and 5,981,421 to McGill et al., which teachings are incorporated herein by reference.

Surface Area Reduction of Silica Particulate "Substrate" Material

Regarding the surface area reduction of above general step 2), after slurrying the crude silica particulate in an aqueous medium, active silica is generated in the same medium for a time period and under conditions sufficient to provide dense amorphous silica deposits on the substrate particulate sufficient to reduce the BET surface area and CPC's potential for binding to it. In general, the slurried crude silica particulate intermediate product is dispersed in an aqueous medium in which active silica is generated by acidulating an alkali metal silicate with a mineral acid therein. The resulting mixture is gently agitated or mixed, such as with a paddle mixer, for a sufficient period of time to ensure that the active silica and substrate silica particulates are substantially uniformly dispersed. The resulting low surface area silica product is filtered or otherwise dewatered, washed, and dried as needed.

In this regard, the methodology used to provide the active silica in the medium that is deposited as an amorphous silica material on the surfaces of the substrate particulate generally involves similar chemistries and conditions applied to make the crude or substrate particulate, except that the addition rates of the silicate and acid used for formation of active silica must be sufficiently slowed in order to insure the active silica deposits on the existing substrate silica particles and does not form separate precipitated particles. The addition of active silica too rapidly will result in the formation of separate precipitated silica particles and will not result in the desired decrease in surface area of the substrate silica. It is desirable to use temperatures ranging from 60 to 100° C., pH from 7 to 10, and an active silica deposition rate such that the specific surface area of the of the silica particulate material is reduced. Optionally, a salt such as $Na_2SO_4$ can be added in an amount such that the desired decrease in surface area is still obtained. Reaction temperatures of greater than 90° C. and pH greater than 9 are preferred for use during the surface area reduction portion of the process.

In one aspect, the surface area reduction process is manipulated appropriately to ensure that the extent of deposition of active silica is at a rate and in an amount effective to provide a BET specific surface area of from 1 to 50 square meters per gram, preferably 1 to 40 square meters per gram, more preferably less than 30 square meters per gram. It also should be in amount effective to reduce binding of CPC thereto as compared to the silica particulate that has not been exposed to a surface area reduction process.

In addition, the inventive precipitated silica product has a % CPC Compatibility value generally of at least 20%, particularly greater than 40%, more particularly greater than 60%, and can be even greater than 70%. The "% CPC Compatibility" characteristic of the silica is determined by a testing procedure explained in the examples that follow.

The resulting low surface area silica also generally has a median particle size ranging between about 1 to about 100 microns, and preferably in one embodiment ranges between about 5 and about 20 microns. The particle size of the silicas is measured using a Horiba Particle Analyzer. Model LA-910 manufactured by Horiba Instruments, Boothwyn, Pa.

The resulting silica product can be spray dried in a similar manner as the treatment performed on the crude freshly prepared silicas. Alternatively, the wet cake obtained can be reslurried, and handled and supplied in slurry form or supplied as a filter cake, directly.

Also, drying of silicas described herein can be effected by any conventional equipment used for drying silica, e.g., spray drying, nozzle drying (e.g., tower or fountain), flash drying, rotary wheel drying or oven/fluid bed drying. The dried silica product generally should have a 1 to 15 wt. % moisture level. The nature of the silica reaction product and the drying process both are known to affect the bulk density and liquid carrying capacity. Further, care must be taken that the drying operation and subsequent operations do not detrimentally affect the structure of the silica obtained in the precipitation stage. The dried low surface area silica product is in a finely divided form. In one particular embodiment, the water content of the precipitated silica-containing fractions is about 25% by weight or more for all times until the drying procedure is performed on the low surface area silica product.

To decrease the size of the dried low surface area silica particles further, if desired, conventional grinding and milling equipment can be used. A hammer or pendulum mill may be used in one or multiple passes for comminuting and fine grinding can be performed by fluid energy or air-jet mill. Products ground to the desired size may be separated from other sizes by conventional separation techniques, e.g., cyclones, classifiers or vibrating screens of appropriate mesh sizing, and so forth.

There are also ways to reduce the particle size of the resulting silica product before isolation and/or during the synthesis of the silica product that affect the size of the dried product or product in slurry form. These include but are not limited to media milling, the use of high shear equipment (e.g. high shear pump or rotor-stator mixers), or ultrasound devices. Particle size reduction carried out on the wet silica product can be done at anytime before drying, but more preferably during formation of the core and/or the deposition of the active silica onto the core. Any particle size reduction done on the dry or wet silica product should be done in a way not to significantly reduce the CPC compatibility of the final product.

The recovery of the dried silica in the present invention does not require silica dewatering and dehydration to be performed with an organic solvent replacement procedure. The isolation of the silica product can be performed from an aqueous medium without occurrence of product degradation.

Dentifrice Compositions

Dentifrices that contain the above-described low surface area silica product offer the benefit that therapeutic agents, such as CPC also can be used which remains at an effective antibacterial level in the dentifrice despite the presence of silica abrasive. The low surface area silica particles show decreased interaction with CPC and as a result there remains an increase in the free CPC in the dentifrice available to improve antibacterial efficacy.

While CPC is used herein as representative of dentifrice therapeutic agents, other antimicrobial agents, (cationic, anionic and nonionic) are contemplated by the invention. Other suitable antimicrobial agents include bisguanides, such as alexidine, chlorhexidine and chlorhexidine gluconate; quarternary ammonium compounds, such as benzalkonium chloride (BZK), benzethonium chloride (BZT), cetylpyridinium chloride (CPC), and Domiphen bromide; metal salts, such as zinc citrate zinc chloride, and stannous fluoride; sanguinaria extract and sanguinarine; volatile oils, such as eucalyptol, menthol, thymol, and methyl salicylate; amine fluorides; peroxides and the like. Therapeutic agents may be used in dentifrice formulations singly or in combination.

As another benefit and advantage, dentifrices containing the low surface area silica product have a superior flavor attributes. The flavor compatibility of the low surface area silica product of this invention is superior to a higher surface area silica material, as has been demonstrated in experiments described herein. Dentifrice compositions incorporating the low surface area silica product described herein generally contain the silica in an effective amount for abrasive and polishing action. This amount can vary, depending on other ingredients of the formulation, for example, but generally will range from about 5 to about 50 wt %.

Dentifrice compositions incorporating the low surface area silica product described herein preferably also contain CPC in an antimicrobial effective amount. This amount can vary, depending on other ingredients of the formulation and limitations placed upon its use by regulating authorities (e.g. FDA), for example, but generally will range from about 0.01 to about 1 wt %., preferably from about 0.1 to about 0.75 wt. %, most preferably from about 0.25 to 0.50 wt. %.

Other additives commonly used or otherwise beneficial in dentifrices also optionally may be included in the formulation. A pharmaceutically acceptable carrier for the components of dentifrice compositions containing the low surface area silica product of the present invention is optional and can be any dentifrice vehicle suitable for use in the oral cavity. Such carriers include the usual components of toothpastes, tooth powders, prophylaxis pastes, lozenges, gums, and the like and are more fully described thereafter.

Flavoring agents optionally can be added to dentifrice compositions. Suitable flavoring agents include oil of Wintergreen, oil of peppermint, oil of spearmint, oil of sassafras, and oil of clove, cinnamon, anethole, menthol, and other such flavor compounds to add fruit notes, spice notes, etc. These flavoring agents consist chemically of mixtures of aldehydes, ketones, esters, phenols, acids, and aliphatic, aromatic and other alcohols.

Sweetening agents, which can be used, include aspartame, acesulfame, saccharin, dextrose, levulose and sodium cyclamate. Flavoring and sweetening agents are generally used in dentifrices at levels of from about 0.005% to about 2% by weight A water-soluble fluoride compound optionally can be added and present in dentifrices and other oral compositions in an amount sufficient to give a fluoride ion concentration in the composition at 25° C., and/or when it is used of from about 0.0025% to about 5.0% by weight, preferably from about 0.005% to about 2.0% by weight, to provide additional anticaries effectiveness. A wide variety of fluoride ion-yielding materials can be employed as sources of soluble fluoride in the present compositions. Examples of suitable fluoride ion-yielding materials are found in U.S. Pat. No. 3,535,421, and U.S. Pat. No. 3,678,154, both being incorporated herein by reference. Representative fluoride ion sources include: stannous fluoride, sodium fluoride, potassium fluoride, sodium monofluorophosphate and many others. Stannous fluoride and sodium fluoride are particularly preferred, as well as mixtures thereof.

Water is also present in the toothpastes and dentifrices according to another embodiment of this invention. Water employed in the preparation of suitable toothpastes should preferably be deionized and free of organic impurities. Water generally comprises from about 2% to 50%, preferably from about 5% to 20%, by weight, of the toothpaste compositions. These amounts of water include the free water which is added plus that which is introduced with other additives and materials, such as humectant.

In preparing toothpastes, it often is necessary to add some thickening or binder material to provide a desirable consistency and thixotropy. Preferred thickening agents are carboxyvinyl polymers, carrageenan, hydroxyethyl cellulose and water-soluble salts of cellulose ethers such as sodium carboxymethyl cellulose and sodium carbokymethyl hydroxyethyl cellulose. Natural gums such as gum karaya, xanthan gun, gum arabic, and gum tragacanth can also be used. Thickening agents in an amount from about 0.5% to about 5.0% by weight of the total composition generally can be used.

Silica thickeners can also be used to modify toothpaste rheology. Precipitated silica, silica gels and fumed silica can be used. Silica thickeners can be added generally at a level of about 5% to about 15%.

It is also often desirable to include some humectant material in a toothpaste to keep it from hardening. Suitable humectants include glycerin (glycerol), sorbitol, polyalkylene glycols such as polyethylene glycol and polypropylene glycol, hydrogenated starch hydrolyzates, xylitol, lactitol, hydrogenated corn syrup, and other edible polyhydric alcohols, used singly or as mixtures thereof. Suitable humectants can be added generally at a level of from about 15% to about 70%.

Chelating agents optionally can be added to the dentifrices of the invention, such as alkali metal salts of tartaric acid and citric acid, or alkali metal salts of pyrophosphates or polyphosphates.

Other optional ingredients and adjuvants of dentifrices, such as those described in U.S. Pat. No. 5,676,932 and Pader, M., Oral Hygiene Products and Practice, Marcel Dekker, Inc., New York, 1988, for instance, also can be added as needed or desired. These other optional adjuvants, additives, and materials that can be added to the dentifrice compositions of the present invention include, for example, foaming agents (e.g., sodium lauryl sulfate), detergents or surfactants, coloring or whitening agents (e.g., titanium dioxide, FD&C dyes), preservatives (e.g., sodium benzoate, methyl paraben), chelating agents, antimicrobial agents, and other materials that can be used in dentifrice compositions. The optional additives, if present, generally are present in small amounts, such as no greater than about 6% by weight each.

In all cases, the ingredients used in dentifrice formulations, such as thickening gums, foaming agents, etc., are selected to be compatible with the therapeutic agents and flavors.

Additionally, while the usefulness of the abrasive cleaning material of this invention is specifically illustrated in oral cleaning compositions, it is will be appreciated that the low surface area silica of this invention has wider usefulness. For instance, it can be used in metal, ceramic or porcelain cleaning or scrubbing and as a CMP (Chemical Mechanical Planarization) polishing agent.

EXAMPLES

The following examples are presented to illustrate the invention, but the invention is not to be considered as limited thereto. In the following examples, parts are by weight unless indicated otherwise.

The following examples 1–10 describe runs in which CPC compatible silica products were produced as part of a single "in situ" continuous production run.

Example 1

40 L of sodium silicate (13%, 3.32 M.R., 1.112 S.G.) was added to a 400-gallon reactor and was heated to 95° C. with stirring at 75 RPM. Sodium silicate (13%, 3.32 M.R., 1.112 S.G.) and sulfuric acid (11.4%) were then simultaneously added to the reactor at rates of 7.8 L/min and 2.3 L/min, respectively, for 47 minutes. After 47 minutes, sodium silicate addition was stopped and the pH was adjusted to 9.5+/−0.2 with continued addition of sulfuric acid (11.4%). (This formed the substrate silica.) Once the pH reached 9.5, sodium silicate (13%, 3.32 M.R., 1.112 S.G.) and sulfuric acid (11.4%) were simultaneously added at rates of 1.1 L/min and 0.4 L/min, respectively, for 300 minutes(active silica addition time). If necessary, the acid rate was adjusted to maintain pH 9.5+/−0.2. After 300 minutes, the flow of sodium silicate was stopped and the pH was adjusted to 5.0+/−0.2 with the addition of sulfuric acid (11.4%) at 2.3 L/min. The batch was digested for 10 minutes at pH 5.0+/−0.2, was filtered, washed to a conductivity<1500 µS, and spray dried.

Example 2

40 L of sodium silicate (13%, 3.32 M.R., 1.112 S.G.) was added to a 400-gallon reactor and was heated to 95° C. with stirring at 50 RPM. Once the temperature stabilized at 95° C., a Silverson in-line mixer coupled to the reactor by a re-circulation line was set to 100 Hz with re-circulation of 100 Hz. Sodium silicate (13%, 3.32 M.R., 1.112 S.G.) and sulfuric acid (11.4%) were then simultaneously added to the reactor at rates of 7.8 L/min and 2.3 L/min, respectively, for 47 minutes. After 15 minutes, the stir rate was increased to 75 RPM. After 47 minutes, the Silverson in-line mixer was stopped. Sodium silicate addition was also stopped and the pH was adjusted to 9.5+/−0.2 with continued addition of sulfuric acid (11.4%). (This formed the substrate silica.) Once the pH reached 9.5, sodium silicate (13%, 3.32 M.R., 1.112 S.G.) and sulfuric acid (11.4%) were simultaneously added at rates of 1.1 L/min and 0.4 L/min, respectively, for 300 minutes (active silica addition time). If necessary, the acid rate was adjusted to maintain pH 9.5+/−0.2. After 300 minutes, the flow of sodium silicate was stopped and the pH was adjusted to 5.0 with the addition of sulfuric acid (11.4%) at 2.3 L/min. The batch was digested for 10 minutes at pH 5.0, was filtered, washed to a conductivity <1500 µS, and spray dried.

Examples 3–6

For these examples, 50 L of sodium silicate (13%, 3.32 M.R., 1.112 S.G.) was added to a 400-gallon reactor and was heated to 95° C. with stirring at 50 RPM. Once the temperature stabilized at 95° C., a Silverson in-line mixer coupled to the reactor by a re-circulation line was set to 100 Hz with re-circulation of 100 Hz. Sodium silicate (13%, 3.32 M.R., 1.112 S.G.) and sulfuric acid (11.4%) were then simultaneously added to the reactor at rates of 9.8 L/min and 2.9 L/min, respectively, for 47 minutes. After 15 minutes, the stir rate was increased to 75 RPM. After 47 minutes, the Silverson in-line mixer was stopped (silica substrate formed) and the flow of sodium silicate (13%, 3.32 M.R., 1.112 S.G.) was adjusted to a specified rate. Once the pH reached 9.5, the sulfuric acid (11.4%) rate was adjusted to maintain pH 9.5+/−0.2. After a specified active silica addition time, the flow of sodium silicate was stopped and the pH was adjusted to 5.0+/−0.2 with the addition of sulfuric acid (11.4%) at 2.9 L/min. The batch was digested for 10 minutes at pH 5.0+/−0.2, was filtered, washed to a conductivity<1500 µS, and spray dried. The specified silicate rate and active silica addition time are given below in Table 1.

TABLE 1

| Example | Adjusted silicate rate, L/min | Active Silica Addition Time, min. |
| --- | --- | --- |
| 3 | 2.8 | 150 |
| 4 | 3.3 | 150 |
| 5 | 3.3 | 120 |
| 6 | 1.8 | 150 |

Figure 2:
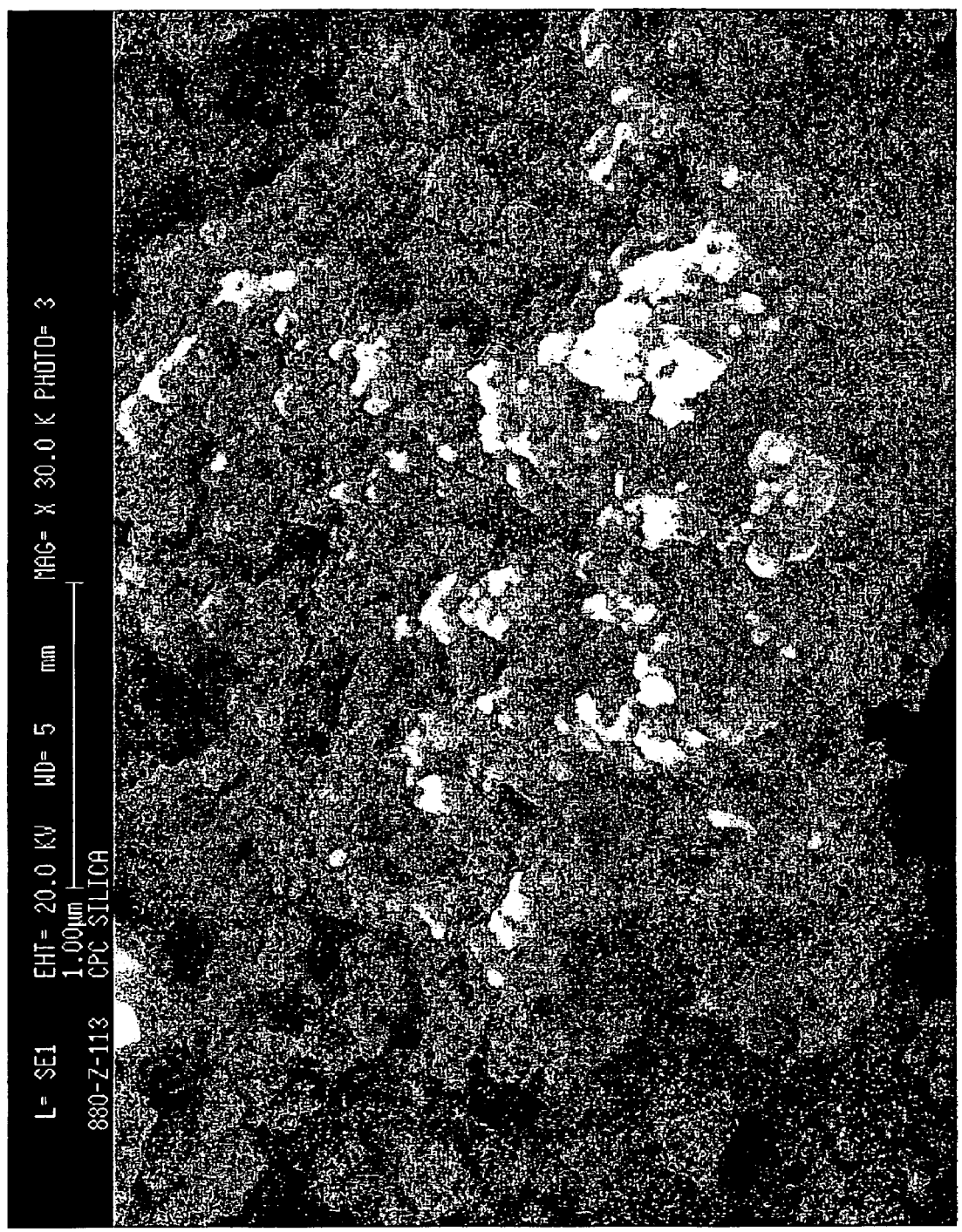
FIG. 2 is an SEM of a commercial silica product, Zeodent® 113, which does not have the surface-treatment.

FIG. 1 is an SEM of a low surface area silica made according to Example 3 described herein. FIG. 2 is an SEM of a commercial silica product, Zeodent® 113.

Example 7

50 L of sodium silicate (13%, 3.32 M.R., 1.112 S.G.) was added to a 400-gallon reactor and was heated to 95° C. with stirring at 50 RPM. Once the temperature stabilized at 95° C., a Silverson in-line mixer coupled to the reactor by a re-circulation line was set to 60 Hz with re-circulation of 100 Hz. Sodium silicate (13%, 3.32 M.R., 1.112 S.G.), sulfuric acid (20.0%) and water were then simultaneously added to the reactor at rates of 11.7 L/min, 1.88 L/min and 1.60 L/min, respectively, for 47 minutes. After 15 minutes, the stir rate was increased to 75 RPM. After 47 minutes, the Silverson in-line mixer was stopped and the flow of sodium silicate (24.4%, 3.32 M.R., 1.227 S.G.) was adjusted to 1.60 L/min (substrate silica formed). The water pump rate was set to 0.0 L/min. Once the pH reached 9.5, the sulfuric acid (20.0%) rate was adjusted to maintain pH 9.5+/−0.2 (~0.79 L/min). After a total batch time of 197 minutes, 150 minutes of which is the active silica addition time, the flow of sodium silicate was stopped and the pH was adjusted to 5.0+/−0.2 with the addition of sulfuric acid (20.0%) at 2.9 L/min. The batch was digested for 10 minutes at pH 5.0+/−0.2, was filtered, washed to a conductivity<1500 µS, and spray dried.

Examples 8–11

For examples 8–11, Example 3 was reproduced up to substrate formation following the step of adjusting the pH to 9.5+/−0.2. The varying active silica addition times are given below in Table 2. Thereafter, a two-gallon aliquot of the reaction mixture was taken to the laboratory. After the temperature was stabilized at 95° C., sulfuric acid (11.4%) was added at a rate of 17 ml/min until pH 5.0+/−0.2 was reached. The reaction mixture was then digested for 10 minutes while maintaining pH 5.0+/−0.2, was filtered, washed with ~7500 ml of distilled water, and was oven dried overnight at 105° C.

TABLE 2

| Example | Active Silica Addition Time (min.) |
| --- | --- |
| 8 | 30 |
| 9 | 60 |
| 10 | 90 |
| 11 | 120 |

A number of properties were measured for the silica products obtained in Examples 1–11, which are summarized in Table 3.

For Examples 1–11, as well as other examples summarized herein, the "CPC Compatibility characteristic value was determined in the following manner.

CPC Compatibility Test 27.00 g of a 0.3% solution of CPC was added to a 3.00 g sample of the silica to be tested. The silica was previously dried at 105° C. to 150° C. to a moisture content of 2% or less, and the pH of the sample was measured to ensure the 5% pH was between 5.5 and 7.5. The mixture was shaken for a period of 10 minutes. Accelerated aging testing requires agitation of the test specimen for 1 week at 140° C. After agitation was complete, the sample was centrifuged and 5 ml of the supernatant was passed through a 0.45 µm PTFE milli-pore filter and discarded. An additional 2.00 g of supernatant was then passed through the same 0.45 µm PTFE milli-pore filter and then added to a vial containing 38.00 g of distilled water. After mixing, an aliquot of the sample was placed in a cuvette (methyl methacrylate) and the U.V. absorbance was measured at 268 nm. Water was used as a blank. The % CPC Compatibility was determined by expressing as a percentage the absorbance of the sample to that of a CPC standard solution prepared by this procedure with the exception that no silica was added.

The "% Active Silica" values were determined by calculation from the batch parameters. Active silica is determined by knowing the volume of active silica used and the silicate concentration, S.G. and M.R. Likewise, the total batch silica is calculated by knowing the total volume of silica used and silicate concentration, S.G. and M.R. % Active silica equals g Active silica divided by g total batch silica times 100. For instance in Example 1:

Silicate used is 13%, 3.32 M.R., 1.112 S.G.

Vol. of active silica=(1.1 l/min) (300 min) =330 liters

Vol. of substrate silica=40 Liters+(7.8 l/min)(47 min)= 406.6 liters

Total silica vol.=330+406.6=736.6 liters $$\% \text{ Active silica} = \frac{(330 \text{ L})(0.13)(1.112)(3.32)(60/261.2)(1000)}{(736.6 \text{ L})(0.13)(1.112)(3.32)(60/261.2)(1000)}$$
$$= 44.80$$

As is seen in the above calculation when computing in situ % active silica, all terms except the volumes cancel so that the % active silica equals the active silica volume/total silica volume. When starting with a premanufactured silica substrate, which is measured in weight values, one must use the above equation to convert active silica to a weight measure, such as grams to put all ingredients on the same basis.

The BET and Linseed Oil Absorption values were determined by procedures described in U.S. Pat. No. 5,981,421, which teachings are incorporated herein by reference.

TABLE 3

| Example | % CPC Compatibility | BET (m²/g) | % H$_2$O | Oil Absorbtion (cc/100 g) | Median Particle Size (µm) | % Active Silica |
|---|---|---|---|---|---|---|
| 1 | 65.0 | 4 | 6.6 | 49 | 13.9 | 45 |
| 2 | 78.2 | 9 | 5.8 | 49 | 7.5 | 45 |
| 3 | 84.8 | 21 | 6.3 | 47 | 10.9 | 45 |
| 4 | 82.8 | 10 | 7.5 | 37 | 9.9 | 55 |
| 5 | 79.1 | 22 | 8.1 | 32 | 7.9 | 45 |
| 6 | 80.6 | 9 | 5.8 | 45 | 5.1 | 35 |
| 7 | 88.0 | 17 | 7.2 | 38 | 8.6 | 45 |
| 8 | 46.2 | 11 | 1.2 | 51 | 5.1 | 14 |
| 9 | 70.9 | 15 | 1.2 | 52 | 5.4 | 25 |
| 10 | 82.0 | 3 | 0.8 | 58 | 6.8 | 33 |
| 11 | 84.4 | 10 | 1.3 | 53 | 8.9 | 40 |

The following Examples 12–17 describe additional runs in which the deposition of the active silica material was performed in situ on a silica substrate particulate as part of a single continuous process flow.

Examples 12–17

Substrate Formation:

Sodium silicate solution (105 ml, 13%, 3.32 M.R., 1.112 S.G.) was added to a one-gallon stainless steel reactor and was heated to 85° C. with stirring at 300 RPM. Sodium silicate (13%, 3.32 M.R., 1.112 S.G.) and sulfuric acid (11.4%) were simultaneously added to the reactor at rates of 20.6 and 6.2 ml/min, respectively, for 47 minutes. After 47 minutes, the flow of silicate to the reactor was stopped and the pH was adjusted to 5.5+/−0.2 with the continued addition of sulfuric acid (11.4%). The reaction mixture was then digested for 10 minutes at 93° C.

Surface Area Reduction:

After the substrate was digested, the pH of the solution was brought to target after digestion pH with the addition of sodium silicate solution (13%, 3.32 M.R., 1.112 S.G.) at target silicate rate and was continued for a specified active silica addition time. During this time the temperature was adjusted to second reaction temperature and maintained at this temperature for the remainder of the batch. Once the target pH was reached, sulfuric acid (11.4%) was added at a specified second acid rate to maintain the target pH during the remainder of the reaction. For the higher pH examples 16–17 the sodium silicate rate was increased to 5.8 ml/min. at this time. If necessary, the flow of acid was adjusted to maintain pH. At the end of the active silica addition time, the addition of acid and silicate was stopped, the final batch pH adjusted, if necessary and the batch was dropped. It was washed with approximately 2 gallons of de-ionized water, and dried in an oven overnight at 105° C. The process variables for examples 12–17 are given in Table 4 below.

TABLE 4

| | Example 12 | Example 13 | Example 14 | Example 15 | Example 16 | Example 17 |
|---|---|---|---|---|---|---|
| pH after substrate digestion | 7 | 7 | 7 | 9 | 9.5 | 9.5 |
| Target silicate rate, ml/min. | 2.4 | 2.9 | 2.4 | 2.4 | 2.9 | 2.9 |
| Active silica addition time, min. | 240 | 300 | 240 | 240 | 150 | 150 |
| 2$^{nd}$ reaction Temp, ° C. | 75 | 75 | 93 | 75 | 95 | 95 |
| 2$^{nd}$ Acid rate, ml/min. | 0.8 | 1.9 | 0.8 | 0.8 | 2.6 | 2.6 |
| Final silicate rate, ml/min. | 2.4 | 2.9 | 2.4 | 2.4 | 5.8 | 5.8 |
| Final pH | 7.0 | 7.0 | 7.0 | 7.0 | 7.0 | 5.5 |

A number of properties were measured for the low surface area silicas of Examples 12–17, which are summarized in Table 5.

TABLE 5

| Example | % CPC Compat. | BET (m²/g) | % H2O | Oil Absorbtion (cc/100 g) | Median Particle Size (µm) | % Active Silica |
|---|---|---|---|---|---|---|
| 12 | 52.2 | 23 | 4.7 | 71 | 32.3 | 35 |
| 13 | 60.5 | 26 | 4.3 | 71 | 49.5 | 45 |
| 14 | 68.2 | 24 | 4.5 | 73 | 32.4 | 35 |

TABLE 5-continued

| Example | % CPC Compat. | BET (m²/g) | % H2O | Oil Absorbtion (cc/100 g) | Median Particle Size (μm) | % Active Silica |
|---|---|---|---|---|---|---|
| 15 | 58.6 | 19 | 4.2 | 69 | 27.1 | 35 |
| 16 | 78.0 | 13 | 4.6 | 53 | 32.2 | 45 |
| 17 | 87.6 | 11 | 4.9 | 48 | 44.0 | 45 |

The following Examples 18–23 describe additional runs in which the deposition of the active silica material was deposited on premanufactured silica powders.

Example 18

Deionized water, specified premanufactured silica (substrate) and optionally anhydrous sodium sulfate were added to a two-gallon stainless steel reaction vessel and taken to a reaction temperature with continuous stirring at 400 RPM. Temperature and stirring rate were held constant for the duration of the batch. Sodium silicate (3.32 molar ratio) and sulfuric acid were added simultaneously at specified rates for a specified reaction time. The sulfuric acid addition rate was adjusted slightly when necessary to maintain the reaction slurry target pH. After the specified reaction time, addition of the sodium silicate was stopped and sulfuric acid was added to a pH of a 5.0±0.2. The resulting reaction media was filtered using a Buchner funnel and washed with approximately 4000 mL of deionized water. The washed, de-watered slurry was then oven dried overnight at 105° C.

TABLE 6

| | Example No. | | | | | |
|---|---|---|---|---|---|---|
| | 18 | 19 | 20 | 21 | 22 | 23 |
| Silica Substrate | Zeodent ® 105 | Zeodent ® 105 | Zeodent ® 114 | Zeodent ® 114 | Zeodent ® 114 | Zeodent ® 114 |
| Substrate % solids | 30 | 30 | 30 | 25 | 25 | 25 |
| Substrate wt, g | 750 | 750 | 750 | 500 | 500 | 500 |
| Water, ml | 1750 | 1750 | 1750 | 1500 | 1500 | 1500 |
| Na2SO4, g | 0 | 0 | 0 | 32 | 0 | 358 |
| Reaction Temp. (° C.) | 75 | 75 | 75 | 95 | 95 | 95 |
| Sodium Silicate Conc. (% Solids) | 13.0 | 13.0 | 13.0 | 13.0 | 13.0 | 24.4 |
| Sodium Silicate addition rate, ml/min | 13.1 | 15.0 | 15.0 | 24.8 | 24.8 | 20 |
| Sulfuric acid Conc. (% solids) | 11.4 | 11.4 | 11.4 | 11.4 | 11.4 | 20.0 |
| Acid addition rate, ml/min. | 4.1 | 4.7 | 4.7 | 6.0 | 7.5 | 5.1 |
| Target pH | 7.0 | 7.0 | 7.0 | 9.5 | 9.5 | 9.0 |
| Simultaneous Addition (min) | 173.9 | 243.5 | 243.5 | 150.0 | 150.0 | 60.0 |
| % Active Silica | 25 | 35 | 35 | 45 | 45 | 35 |

TABLE 7

| | Example No. | | | | | |
|---|---|---|---|---|---|---|
| | 18 | 19 | 20 | 21 | 22 | 23 |
| % CPC Compatibility | 45.0 | 70.6 | 27.2 | 55.0 | 49.3 | 24.7 |
| % Active Silica | 25 | 35 | 35 | 45 | 45 | 35 |
| % H2O | 3.59 | 3.94 | 5.83 | 3.10 | 1.80 | 1.60 |
| BET Surface Area (m2/g) | 15 | 7 | 23 | 3 | 12 | 14 |
| Oil Absorption (ml/100 g) | 46 | 45 | 78 | 69 | 67 | 81 |
| Median Particle Size (μm) | 7.0 | 6.5 | 5.6 | 7.7 | 6.9 | 7.4 |

FLAVOR COMPATIBILITY STUDIES

Experimental studies were performed to assess the flavor compatibility of low surface area silica product representative of this invention.

Procedure for Flavor Compatibility Analysis:

Sample Preparation:

0.5 g samples of a silica product were weighed to 2 decimal place accuracy and loaded into 15 ml amber glass screw top with polypropylene hole cap vials w/PTFE/Silicone septa (available from Supelco part # 27049). Using a gas tight syringe, 10 μLs of a Natural Spearmint Essential Oil (Available from Sigma Aldrich Cat. # W30322-4) was added to the samples, taking care to evenly distribute the oil on the sample, and not to wet the inside of the glass vial with the oil. The vials were then capped and the samples agitated on a vortex mixer for approximately 10 seconds to ensure A number of properties were measured for the silica products obtained for Examples 18–23, which are summarized in Table 7.

even distribution of the oil on the sample. The samples were then allowed to equilibrate prior to analysis at room temperature, 22.5 to 23.5° C., for about 12 hours. The samples were not agitated immediately prior to analysis. Two specimens were tested for each sample and the results averaged.

Headspace Sampling:

The samples were then sampled for 5 minutes at room temperature using a 65 μm Polydimethylsiloxane-Divnylbenzene Solid Phase microextraction (SPME) fiber (Available from Supelco, #57310-U) and a manual fiber holder assembly (Supelco #57330-U). Room temperature was maintained between 22.5 and 23.5C during the analysis. After a 5-minute exposure, the fiber was withdrawn from the sample vial and desorbed into the GCMS system and analyzed under the following conditions.

Chromatography Conditions:

A Hewlett Packard 5890 GC with 5972 Mass Selective Detector was used for this analysis.

Column: Restek Stabilwax, 60 m, 0.25 mmID, 0.25 μgm film

Injection: 250° C., 25 ml/min split, 1 mm split liner

Carrier: He 28 cm/sec @ 100° C.

Oven Program:

50° C., hold 4 minutes

4° C./min to 100° C., hold 0 minutes

8° C./min to 200°, hold 0 minutes

25° C./min to 240° C., hold 4 minutes

Detector: MS 280° C., scan mode, 30-550AMU.

The oil of spearmint reference was prepared in the same manner as described above, except without the addition of any silica. Ten of the major oil of spearmint constituent peaks were chosen for data collection to evaluate the effect of different silicas on the intensity of these flavor components. It is theorized that a change in peak intensity of some of the flavor components is proportional to changes in perceived flavor.

Example 24

Flavor compatibility data was collected for samples of spearmint oil standard, silica product made according the procedures described in Example 3 and for Zeodent® 113 silica for purposes of having their flavor compatibility assessed in the manner described above, and the data is summarized below in Table 8.

TABLE 8

| | Std. Oil | Zeodent 113 silica | | Ex. 3 | |
|---|---|---|---|---|---|
| Peak ID | Peak Area × $10^4$ | Peak Area × $10^4$ | % change from oil | Peak Area × $10^4$ | % change from oil |
| a-pinene | 870 | 668 | −23.2 | 831 | −4.6 |
| b-pinene | 852 | 739 | −13.8 | 833 | −3.1 |
| myrcene | 2502 | 2226 | −12.4 | 2421 | −3.7 |
| limonene | 14722 | 14648 | −1.7 | 14602 | −0.8 |
| eucalyptol | 2121 | 200 | −91.2 | 1800 | −15.0 |
| 3-octanol | 657 | 30 | −95.4 | 575 | −12.6 |
| b-terpineol | 389 | 9 | −97.8 | 324 | −16.4 |
| menthone | 316 | 45 | −85.9 | 343 | 8.5 |
| dihydrocarvone | 1087 | 211 | −80.7 | 1315 | 21.0 |
| carvone | 19920 | 3951 | −80.0 | 24317 | 22.0 |

For these tests, the temperature of the room was controlled between 22.5 and 23.5° C. throughout the data collection. As can be seen, the inventive low surface area silica product had much less effect than higher surface area Zeodent 113 silica on the various major components of a typical toothpaste flavor and therefore would provide increased flavor compatibility.

It will be understood that various changes in the details, materials, and arrangements of the parts which have been described and illustrated herein in order to explain the nature of this invention may be made by those skilled in the art without departing from the principles and scope of the invention as expressed in the following claims.

What is claimed is:

1. A precipitated silica product comprising silica particulate comprising silica particles having a median diameter of 1 to 100 micrometers that support surface deposits thereon comprising an active precipitated amorphous silica material present in an amount effective to provide a BET specific surface area of from 1 to 50 square meters per gram for the silica particulate and present in an amount effective to reduce attachment of cetylpyridinium chloride to the silica particulate as compared to the silica particulate without the surface deposits.

2. A precipitated silica product comprising silica particulate comprising precipitated silica particles having a median diameter less than 100 micrometers, a BET specific surface area of from 1 to 50 meters per gram for the silica particulate and a percentage cetylpyridinium chloride (%CPC) compatibility of greater than approximately 20%.

3. A precipitated silica product according to claim 2, wherein the silica particulate has a BET specific surface area of from 1 to 40 square meters per gram for the silica particulate and a %CPC compatibility of greater than approximately 40%.

4. A predcipitated silica product according to claim 2, wherein the silica particulate has a BET specific surface area of less than approximately 35 square meters per gram for the silica particulate and a %CPC compatibility of greater than approximately 60%.

5. A precipitated silica product according to claim 2, wherein the silica particulate a BET specific surface area of less than approximately 30 square meters per gram for the silica particulate and a %CPC compatibility of greater than approximately 70%.

6. A precipitated silica product according to claim 2, wherein the silica particles have a median diameter of 1 to 20 micrometers.

7. A precipitated silica product according to claim 2, wherein the precipitated silica product has a %CPC compatibility value of approximately 20 to 95%.

8. A precipitated silica product according to claim 2, wherein the precipitated silica product has a %CPC compatibility value of at least 40%.

9. A precipitated silica product according to claim 2, wherein the precipitated silica product has a %CPC compatibility value of at least 60%.

10. A precipitated silica product according to claim 2, wherein the precipitated silica product has a %CPC compatibility value of at least 70%.

11. A precipitated silica product according to claim 2, wherein the silica particulate comprises silica aggregates or agglomerates individually comprising unitary clusters of a plurality of the silica particles.

12. A dentifrice comprising a precipitated silica product comprising silica particulate comprising precipitated silica particles having a median diameter less than 100 micrometers, a BET specific surface area of from 1 to 50 square meters per gram for the silica particulate and a percentage cetylpyridinium chloride (%CPC) compatibility of greater than approximately 20%.

13. Dentifrice according to claim 12, wherein the silica particulate has a BET specific surface area of from 1 to 40 square meters per gram for the silica particulate.

14. Dentifrice according to claim 12, wherein the precipitated silica product has a %CPC compatibility value of approximately 20% to 95%.

15. Dentifrice according to claim 12, wherein the precipitated silica product has a %CPC compatibility value of at least 40%.

16. Dentifrice according to claim 12, wherein the precipitated silica product has a %CPC compatibiity value of at least 60%.

17. Dentifrice according to claim 12, wherein the silica particulate comprises silica aggregates or agglomerates individually comprising unitary clusters of a plurality of the silica particles.

18. Dentifrice according to claim 12, further including an effective amount of at least one flavorant compatible with CPC.

19. Dentifrice according to claim 12, further including an effective amount of an anticaries compound comprising a fluoride ion source.

20. Dentifrice according to claim 12, further including an effective amount of an antimicrobial agent.

21. A dentifrice comprising a) an antibacterial effective amount of cetylpyridinium chloride; and b) a precipitated silica product comprising silica particulate comprising silica particles having a median diameter of 1 to 100 micrometers that support surface deposits thereon comprising an active precipitated amorphous silica material present in an amount effective to provide a BET specific surface area of from 1 to 50 square meters per gram for the silica particulate and present in an amount effective to reduce attachment of celylpyridinium chloride to the silica particulate as compared to the silica particulate without the surface deposits, such that the cetylpyridinium chloride remains at an effective antibacterial level in the dentifrice.

22. A dentifrice according to claim 21 comprising a precipitated silica product comprising silica particulate comprising silica particles having a median diameter less than 100 micrometers, a BET specific surface area of from 1 to 5square meters per gram for the silica particulate and wherein the silica particulate provides a superior flavor compatibility as compared to the dentifrice containing the silica particulates without the surface deposits.

23. A process for making a precipitated silica product comprising:

a) providing a silica particulate comprising precipitated amorphous silica particles having a median diameter of 1 to 100 micrometers; and subsequently b) depositing active silica onto the surface of the substrate silica particulate by acidulation of an alkali metal silicate in an aqueous medium, in which the substrate silica particulate is dispersed, in an amount effective to provide a slurry of low surface area silica particulate having a BET specific surface of 1 to 50 square meters per gram and effective to reduce attachment of cetylpyridinium chloride to the resulting silica particulate as compared to the silica particulate without the active silica deposition step.

24. The process of claim 23, further comprising dewatering and drying the silica particulate to a flowable finely divided particulate form.

25. The process of claim 23, wherein the providing of the silica particulate comprises slurrying a dry flowable particulate form of the silica particulate in an aqueous solution.

26. The process of claim 23, wherein the providing of the silica particulate of step "a" comprises forming the silica particulate in situ by acidulation of an alkali metal silicate in an aqueous medium without drying the silica particulate below 20 wt% water content before initiating the silica deposition of step "b" thereof.

27. The process of claim 23, wherein the deposition of active silica deposits onto silica particulate to provide a slurry of low surface area silica particulate proceeds to an extent providing a BET surface area of from 1 to 40 square meters per gram for the silica particulate.

28. The process of claim 23, wherein the providing of the silica particulate comprises providing silica aggregates or agglomerates individually comprising unitary clusters of a plurality of the precipitated amorphous silica particles.

29. The process of claim 23, wherein the precipitated silica product provided has a %CPC compatibility value of approximately 20 to 95%.

30. The process of claim 23, wherein the precipitated silica product provided has a %CPC compatibility value of at least 40%.

31. The process of claim 23, wherein the precipitated silica product provided has a %CPC compatibility value of at least 60%.

32. The process of claim 23, wherein the precipitated silica product provided has a %CPC compatibility value of at least 70%.

33. The product of the process of claim 23.

* * * * *